United States Patent [19]

Dorsey, III

[11] Patent Number: 5,391,145
[45] Date of Patent: Feb. 21, 1995

[54] IRRIGATION CONTROL VALVE FOR ENDOSCOPIC INSTRUMENT

[76] Inventor: James H. Dorsey, III, 2117 NE. 44th St., Lighthout Point, Fla. 33064

[21] Appl. No.: 20,062

[22] Filed: Feb. 19, 1993

Related U.S. Application Data

[63] Continuation-in-part of Ser. No. 470,771, Jan. 26, 1990, Pat. No. 5,188,591.

[51] Int. Cl.⁶ ............................................. A61M 1/00
[52] U.S. Cl. ......................................... 604/33; 604/35; 604/249; 137/596.2; 251/325
[58] Field of Search .................................. 604/27–35, 604/38–40, 118, 119, 121, 128, 173, 246, 249, 902, 256, 258; 137/596, 596.2, 883; 91/454; 128/4 A; 251/325

[56] References Cited

U.S. PATENT DOCUMENTS

| | | | |
|---|---|---|---|
| 2,112,629 | 3/1938 | Lloyd | 604/249 |
| 4,248,589 | 2/1981 | Lewis . | |
| 4,408,598 | 10/1983 | Ueda | 128/4 A |
| 4,537,182 | 8/1985 | Otani | 251/325 |
| 4,537,209 | 8/1985 | Sasa | 128/4 A |
| 4,548,197 | 10/1985 | Kinoshita | 604/27 |
| 4,552,130 | 11/1985 | Kinoshita | 128/4 A |
| 4,667,655 | 5/1987 | Ogiu et al. | 604/27 |
| 4,748,970 | 6/1988 | Nakajima | 128/4 A |
| 4,925,450 | 5/1990 | Imonti et al. | 604/902 |
| 4,957,483 | 9/1990 | Gonser et al. | 604/30 |

Primary Examiner—C. Fred Rosenbaum
Assistant Examiner—Mark Bockelman
Attorney, Agent, or Firm—Malin, Haley, DiMaggio & Crosby

[57] ABSTRACT

An irrigation control valve for endoscopic instruments is herein described wherein the valve body is bilaterally symmetrical and includes a housing, a plurality of valve chambers, pistons for reciprocal movement within each of said chambers, an inlet port for connection to a source of an irrigation fluid and a vacuum port for connection to a source of vacuum and symmetrical opposed fittings for mounting a probe in either one of two positions to accommodate both the right handed and left handed clinician. The design of both the pistons and valve body are unique, compatible with injection molding fabrication techniques and further provide for replacement and/or into change of the probe. Such interchange and/or replacement of the probe can be accomplished without clamping off of either the source of irrigation fluid or the source of suction because of the proximal location of the probe connection to the valve body relative to both the irrigation and suction valves. The valve body can be used in conjunction with a variety of probes and in various endoscopic procedures; one of the preferred applications of this invention being in the hydrodissection of tissue in/during laparoscopy.

9 Claims, 6 Drawing Sheets

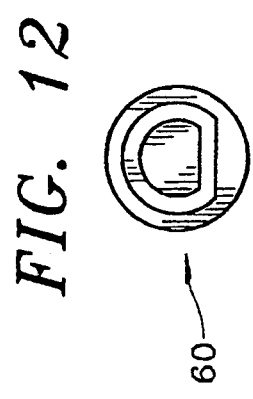
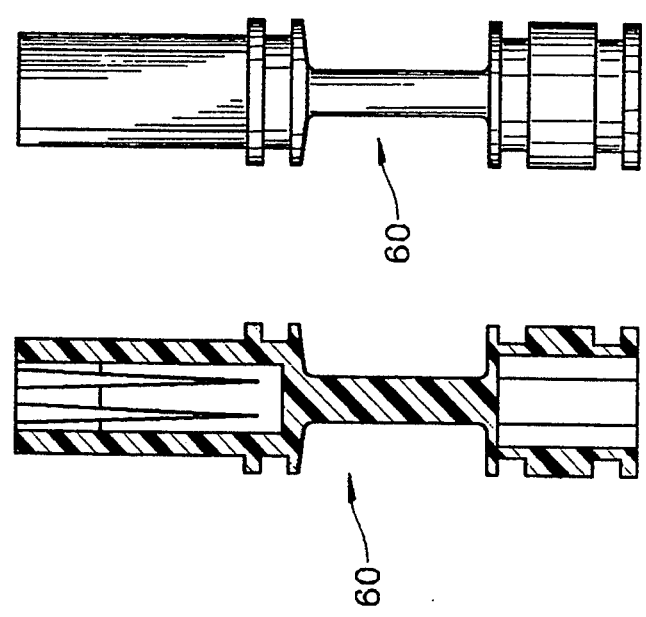
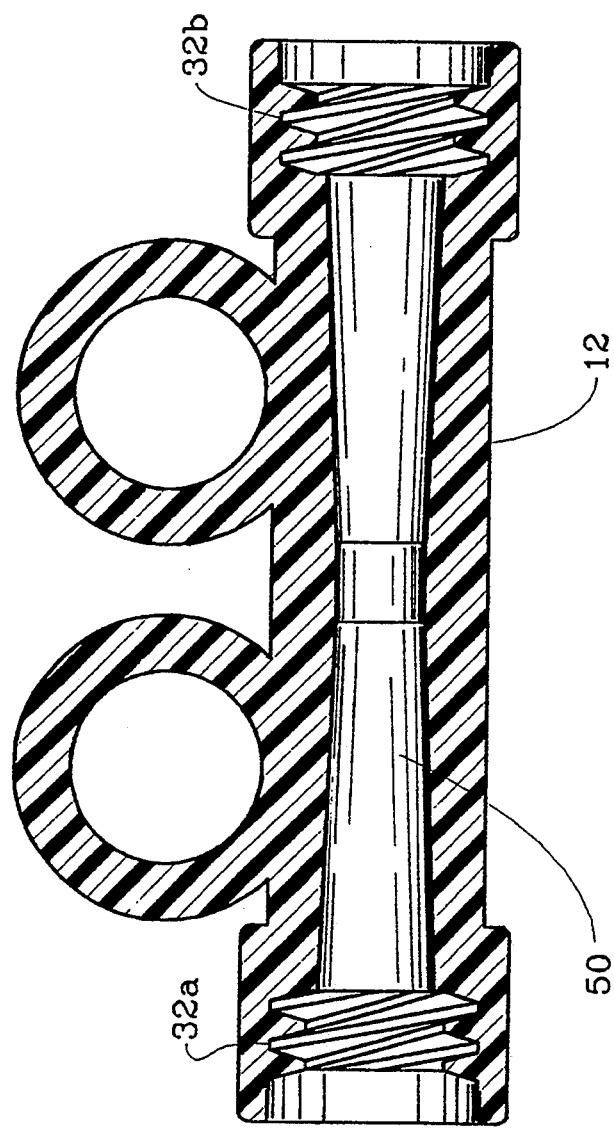
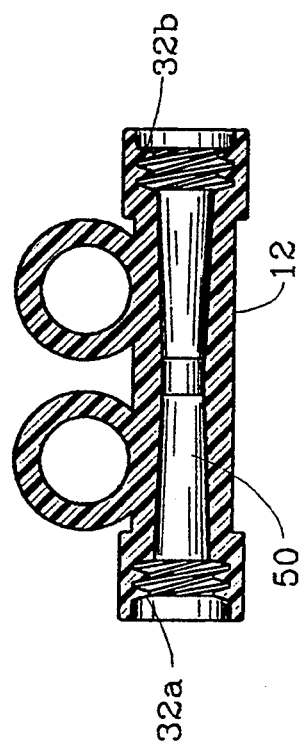

ary of the commercially available endoscopic devices, irrigation has and remains at a relatively primitive level of sophistication. This is also the case in the endoscopic instruments specifically designed for hydrodissection. All of these devices are generally limited in that the design is biased in favor of either a right or left handed individual; the probe tip has been permanently affixed to the valve body and the probe tip cannot be removed and/or changed. If a different probe tip was required the total device would have to be changed which requires separate closure of both irrigant and suction lines. Upon completion of the operative procedure, the valve with the probe tip are not typically discarded as they are intended for reuse after cleaning and re-sterilization. It is, therefore, to the effective resolution of the aforementioned problems and shortcomings that the present invention is directed.

IRRIGATION CONTROL VALVE FOR ENDOSCOPIC INSTRUMENT

BACKGROUND OF THE INVENTION

This is a continuation-in-part of application Ser. No. 07/470,771, filed Jan. 26, 1990, now U.S. Pat. No. 5,188,591.

FIELD OF THE INVENTION

The present invention relates generally to surgical instruments and more specifically to a suction and irrigation control valve for use in Laparoscopic surgery used in conjunction with probe tip cannula attachments, an endoscopic instrument system incorporating the improved suction and irrigation control valve and to a method for hydrodissection of tissue.

DESCRIPTION OF THE PRIOR ART

The field of endoscopy and the problems associated therewith are well-known. Whether the endoscope is equipped with a telescope and light source or is rigid or flexible, one problem is generally common to both types of systems—the difficulties encountered in the infusion and suction of fluid for clearance of the operative field and the lack of adequate instrumentation to address this problem.

The following patents are representative of endoscopic instruments available to the clinician and the various applications thereof: U.S. Pat. Nos. 4,191,191 to Auburn; 3,967,625 to Yoon; 4,824,434 to Seitz, Jr.; 4,735,194 to Stiegmann; 4,795,424 to Burner; 4,504,493 to Marshall et al.; 4,493,320 to Treat; 4,423,727 to Widran et al. and 4,217,891 to Carson.

The controlled irrigation of an operative field during endoscopy/laparoscopy typically involves regulation of the flow rate of the irrigant fluid through a tube (cannula) by means of conventional stop cock valves or a mechanical equivalent, see for example U.S. Pat. No. 4,795,424 to Burner; 4,493,320 to Treat; 4,423,727 to Widran et al. and 4,217,891 to Carson.

In the state of the art for endoscopic devices presently in use, suction/irrigation has typically been subordinated in both sophistication and importance to the surgical implements which are used with these devices, with the possible exception of the field of hydrodissection. In hydrodissection, a pressurized irrigation fluid is directed through a cannula onto the operative field to separate and delineate planes of tissue and to dissect these tissues the path of least resistance and effect removal of a target tissue. Alternating activation of the irrigation and suction valves effects removal of the infused fluid, fluid endogenous to the operative field and any tissue or debris that has been hydraulically displaced. In the field of hydrodissection, the endoscopic instrument generally consists of a valve body having means for connection (usually a luer lock) to both a source of irrigation fluid and a source of suction. In this type of instrument, a cannula has been permanently affixed to the valve body providing the means for direction of the fluid onto the operative field. Due to the fact that the irrigation fluid is being used for hydrodissection of tissues the cannula of choice would not be of the same configuration as that needed for effective suction and would therefore not contain holes at the end of the cannula. This would allow better direction of forced irrigation on the target tissue to aid in hydro-dissection. Suction holes in a cannula allow water pressure to escape and make this procedure more difficult.

As is evident from review of the commerci

SUMMARY OF THE INVENTION

The present invention provides an irrigation control valve which is bilaterally symmetrical; that is symmetrical along the plain coincident with attachment positions of a probe tip cannula to the valve body and symmetrical along the plain between the two valves. As noted hereinabove, the unique design of this irrigation control valve lends itself to plastic injection molding techniques and, because of its unique symmetrical design, permits the attachment of a selected probe tip cannula to the valve body at either one of two positions, depending upon clinician preferences. The valve body is a relatively simple structure having a plurality of cylinders, each of which is provided with a corresponding piston. Each of these cylinders is further provided with an orifice. In the case of the fluid control valve, the orifice of the cylinder is simply a continuation of the conduit formed by the fitting which is adapted to connection to the source of irrigation fluid. Similarly, the inlet orifice for the suction control valve is simply a continuation of the conduit of the fitting adapted for connection to the source of suction. The cylinder is provided with a second orifice which provides for communication between the cylinder and a second (common) conduit. This common conduit is disposed at right angles to the longitudinal axis of the cylinder. The common conduit is adapted at both ends with a fitting for connection to a probe. The vacuum control cylinder is similarly provided with an orifice which provides for communication between the interior of the cylinder to-a source of vacuum and a second orifice, which provides communication between the interior chamber of the cylinder and the common conduit. Both in the cylinder for the fluid control valve and in the cylinder for the vacuum control valve, the inlet orifice and the orifice to the common conduit are offset relative to one and other. The irrigation control valve is further provided with a reciprocating piston for each cylinder. The construction of the piston for each cylinder is substantially the same in that the barrel of the cylinder is provided with conduit flow path which extends between a first barrel seal to a second barrel seal. Upon reciprocation of the piston within the cylinder, the valve is opened by effecting communication between the inlet orifice and the orifice to the common conduit through the flow path in the barrel of the piston. The degree to which the piston is reciprocated within the cylinder modulates the flow between the inlet orifice and the orifice to the common conduit, be that flow of irrigation fluid or degree of vacuum. A third seal is provided at the base of the cylinder to prevent fluid from accumulating between the end of the piston and the portion of the valve body chamber in which the spring is contained.

The design and construction of the irrigation control valve, most notably the positioning (offset) of the orifice from the inlet port relative to the orifice to the common conduit and the shape of the opening within the barrel of the piston provide this valve with the unique capability of simplicity in manufacture and enhancement in control of flow and/or suction between the common conduit and the port which connects the respective chambers of the valve to the source of irrigation fluid and to the source of suction.

The design of the improved irrigation control valve lends itself to injection molding techniques and is also unique in its ready adaptation to both right and left handed operation due to the symmetry of the valve body and the adaptation of the valve body to interchangeable probe tips. Accordingly, the probe can be mounted in either one of two positions to accommodate the clinician's preference.

Accordingly, the primary object of the present invention to provide an endoscopic instrument system equipped with an irrigation control valve having a symmetrical valve body and interchangeable probe tips.

It is another object of the present invention is to provide an irrigation control valve having a design compatible with plastic injection molding techniques.

It is a further object of the present invention to provide an endoscopic instrument incorporating a symmetrical irrigation control valve which can be readily configured for right or left handed operation, depending upon the replacement and/or connection of the probe tip.

It is still a further object of the present invention to provide an endoscopic instrument system incorporating a symmetrical irrigation control valve having interchangeable probes and a method for the use of such endoscopic system in hydrodissection procedures.

It is yet another object of the present invention to provide an endoscopic instrument which is relatively low in cost and easy to manufacture.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention may be better understood by reference to the drawings in which:

FIG. 9 is a sectional view showing an alternative embodiment for the common conduit;

FIG. 10 is a top sectional view of the present invention showing the alternative embodiment for the common conduit;

FIG. 11 is a front view of an alternative embodiment for the piston of the present invention;

FIG. 12 is a top view of the piston of FIG. 11;

FIG. 13 is a cross sectional view of the piston of FIG. 11.

DETAILED DESCRIPTION OF THE INVENTION

Figure 1:
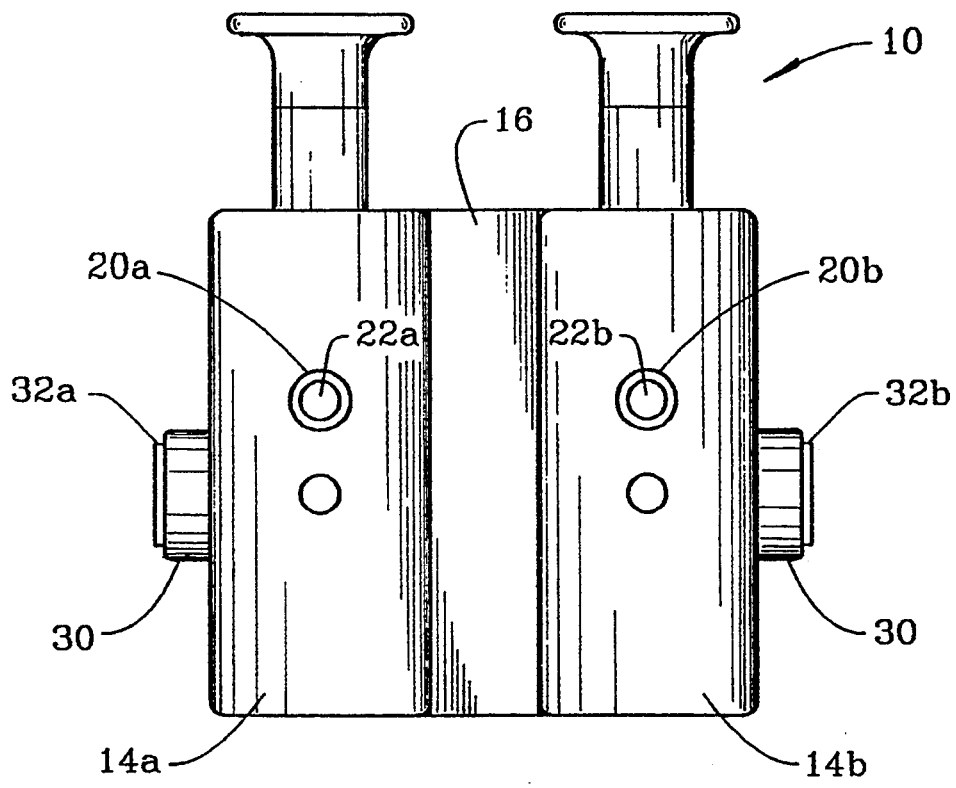
FIG. 1 is a plan view of a symmetrically irrigation control valve of the present invention.

The preferred embodiments of this invention are illustrated in reference to the foregoing enumerated figures. For ease of discussion and simplification of description, a common reference numeral is assigned to a particular component feature of the irrigation control valve and such common reference numeral used within each of the figures.

In the illustration of this invention shown in FIG. 1, the irrigation or control valve (10) comprises a valve housing or body (12) having two valve chambers (14a, 14b), respectively, one valve chamber adapted for communication between a common conduit (30) of control valve (10), a source of irrigation fluid (not shown) and a second valve chamber for communication between a source of suction (not shown) and common conduit (30). In each instances, common conduit (30) of control valve (10) is provided with a probe (not shown). This probe can be connected to either the right hand or left hand fitting located on the side of control valve (10) o The positioning of the probe relative to body (12) of control valve (10) will be based upon clinician preference (whether the clinician is right handed or left handed). In either instance control valve (10) will operate essentially the same. It is also important to note that in this first embodiment illustrated herein either chamber (14a, 14b) of control valve (10) can be connected to either a source of vacuum or a source of irrigation fluid in that both chambers, and, thus, in this embodiment, are essentially the same. In each instance the irrigation control valve (10) of the present invention comprises a valve housing or body within which are formed two cylindrical valve or piston chambers (26a and 26b). The housing of the control valve is further equipped with a pair of fittings (20a, 20b) for each chamber which defines a conduit (22a, 22b). The fitting can be connected to a source of vacuum or a source of irrigation fluid. These conduits (22a, 22b) provide communication between the source of vacuum and/or irrigation fluid and the interior of the valve chamber which is formed within body (12) of control valve (10). The valve chamber can be essentially uniform in diameter and of a defined length. However, but in a preferred embodiment the valve chamber's diameter is stepped to allow for injection molding techniques and also allows for better O-ring functioning, as the O-ring crosses the port and is a smaller diameter and is therefore less likely to be ripped, damaged or worn.

Figure 2:
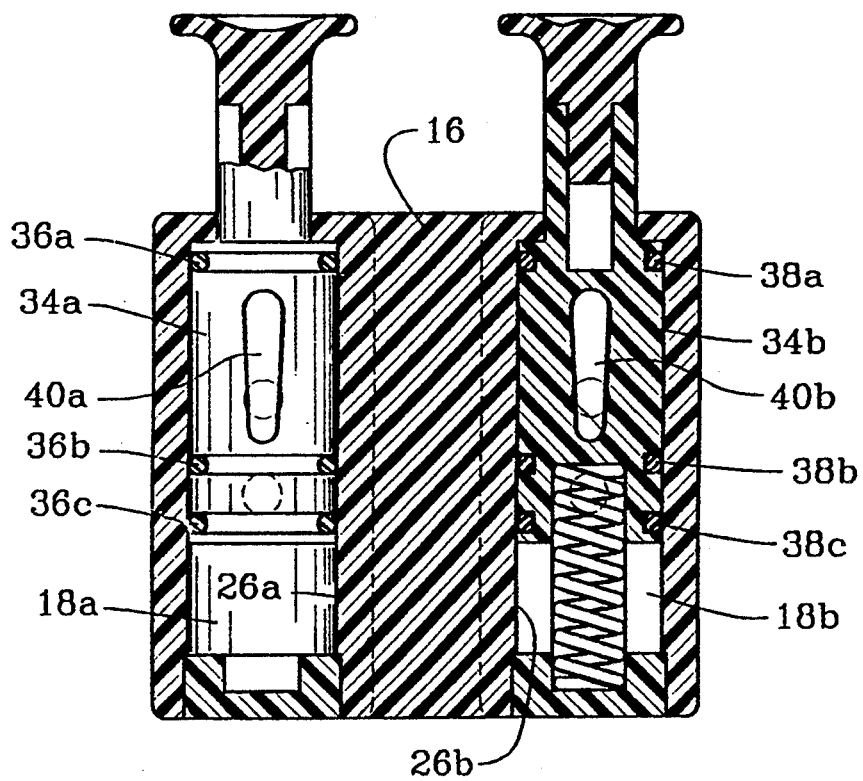
FIG. 2 is a sectional view, taken along the horizontal plane, of the irrigation control valve of FIG. 1.
Figure 5A:
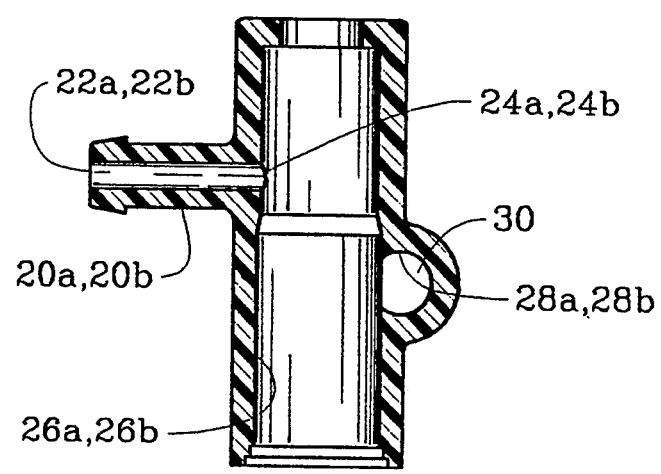
FIG. 5a is a sectional view of the preferred embodiment for the irrigation control valve.
Figure 5:
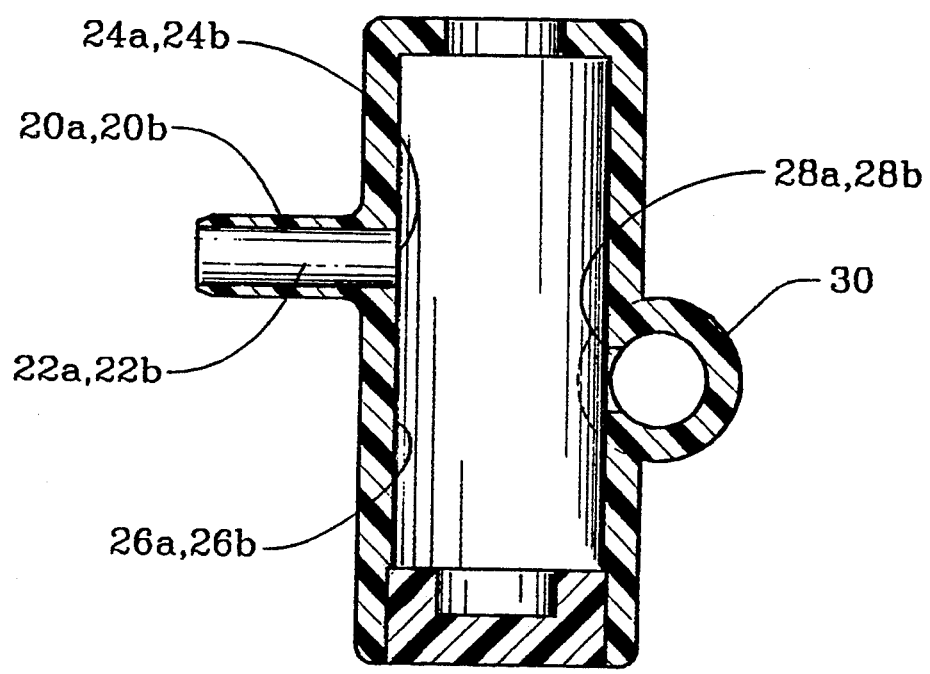
FIG. 5 is a sectional view of the irrigation control valve of FIG. 1, taken along the section lines A—A.

As more completely illustrated in FIGS. 2 and 5, valve body (12) defines two interior cylindrical chamber (18a, 18b) each of which is essentially the same in both dimension and in its contemplated operation. Each such chamber is of a defined length. The fitting or inlet port on the valve body defines a conduit which terminates as an inlet orifice (24a, 24b) in the chamber wall (26a, 26b). The chamber wall is provided with yet a second orifice (28a, 28b), offset from the inlet orifice. This second orifice provides for communication between the interior of the chamber and conduit (30) which is at right angles to the orientation of the chamber. Conduit (30) is provided on either end with a fitting (32a, 32b) adapted to connect to an interchangeable probe tip (70, see FIG. 14).

Common channel or conduit (30) associates with the piston channel via intersection without a through port. Common channel (30) and the piston chambers (26a and 26b) intersect through a core pin design. The core pin which makes the cylinder of chamber (26a and 26b) is intersected and notched with a core pin the makes conduit (30). In this manner these two conduits interface without the need to drill a hole in the valve body. The intersections of the cores creates an elliptical opening in each cylinder and eliminates the need for any drilling.

As seen in FIG. 5a, in the preferred embodiment, the piston chamber is stepped so that a larger inside diameter is at the open end and decreases in size to a smaller inside diameter in through which the stem protrudes. This allows the pull of the core pin during injection molding to be accomplished without utilizing the traditional draft that would change the inside diameter from one side to the other. This reduced diameter allows seal or O-ring (38a) to pass by the port (28a and 28b), without touching it. This prevents seal or O-ring (38a) from being damaged, torn or wearing during surgery.

Figure 3:
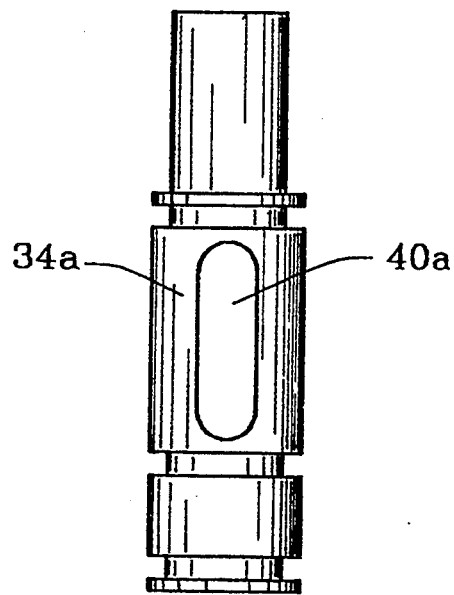
FIG. 3 is a plan view of an alternative embodiment for the piston.
Figure 4:
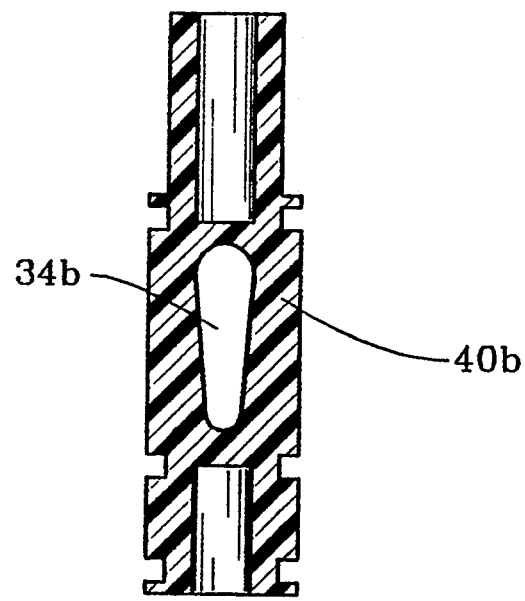
FIG. 4 is a sectional view, along the horizontal plane of the piston of FIG. 3.

Each of the valve chambers within valve body (12) is further provided with a piston (34a, 34b). As more fully illustrated in FIGS. 2, 3 and 4, these pistons are designed for reciprocating movement within the cylinder. In order to provide for watertight and airtight operation, pistons (34a, 34b) are each equipped with a series of seals (36a-c, 38a-c, respectively). Each piston is further provided with an oval opening (40a, 40b, respectively) approximately equivalent in width to the orifices in the chamber wall. The length of the piston is such as to allow reciprocating movement within the cylindrical chamber and accommodation of spring bias means (37a and 37b, see FIG. 6) within the cylinder chamber between the base of the piston and the bottom of the cylindrical chamber. The spring bias means is intended to maintain the valve in the closed portion.

Figure 2A:
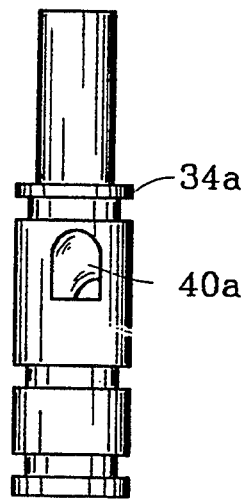
FIG. 2a is a perspective view of the preferred embodiment for the piston of the irrigation control valve.

In the preferred embodiment for the piston (FIG. 2a), oval openings (40a and 40b) of pistons (34a and 34b, respectively) define an essentially "S" shaped flow through. This "S" shaped flow through allows for more precise control of irrigation and is less likely for clogging or sticking due to the fact that there is a greater surface area for lubrication. Furthermore, the seat for seal or O-ring (38a) is smaller that the seat for seal or O-ring (38b or 38c), due to the smaller internal diameter of chambers (26a and 26b) at the top.

The seals which are located both fore (36a, 38a) and aft (36b, 38b) to the oval opening (40a, 40b) in the piston prevent fluid from inadvertently flowing from the source of irrigation fluid to the common conduit. As the cylinder is depressed (in the direction indicated by the arrow), and the oval opening in the piston aligned to permit communication between the inlet orifice and the orifice to common conduit (30), fluid will begin to flow therebetween. The seal at the base of the piston ensures against fluid being trapped between the base of the piston and the base of the valve chamber which, if not vented, could prevent depression of the piston within the chamber.

FIG. 5 illustrates the relative positioning of the two orifices within each cylinder wall and the contemplated direction of flow of fluid upon reciprocal movement of the piston to allow for such flow.

Thus, not only is the valve symmetrical, but the relative arrangement of the valve chamber orifices, piston and associated seals. More specifically, the seals associated with the piston are arranged so as to not only prevent leakage of fluid from the valve, but also communication between the inlet orifice and the orifice to the common conduit, through an elongated opening in the barrel of the piston. The degree to which the piston is reciprocated within this cylinder modulates the flow between the inlet orifice and the orifice to the common conduit. This is effected through a unique combination of the unconventional shape of the opening in the barrel of the piston and arrangement of the seals (which are judiciously positioned on the piston). Upon reciprocating movement of each piston within its respective cylinders, the intermediate seal traverse the inlet orifice. The same is true with respect to seals (36c) and (38c) relative to the orifice which communicates the interior of the chamber to conduit (30). The association of these seals with the piston in the foregoing manner, and the reciprocating movement thereof in relation to both the inlet port and the channel, allows controlled flow of fluid through the valve body. This structure is unique in that it not only provides for cross-orifice travel of the seal (upon reciprocating movement of the piston within the chamber), but also controlled (modulated) flow of fluid, depending upon the degree of depression of the piston in the valve chamber.

The orifices are offset in an axial direction, i.e. a direction along with the piston moves. The aperture in the piston communicates the orifices upon reciprocation.

In operation of valve (10), a conduit is connected to each of the fittings on valve body (12). The conduit can be connected to either a source of irrigation fluid or to a source of vacuum. For the purpose of simplification of description, it is assumed the conduit is connected to a source of irrigation fluid. Upon depression of the piston, the oval shaped opening in the piston barrel effects communication between the inlet orifice and the piston wall and the orifice of the common conduit thereby allowing for flow of fluid therebetween. The further the piston is depressed within the valve chamber, the greater the flow of fluid therethrough.

Figure 7A:
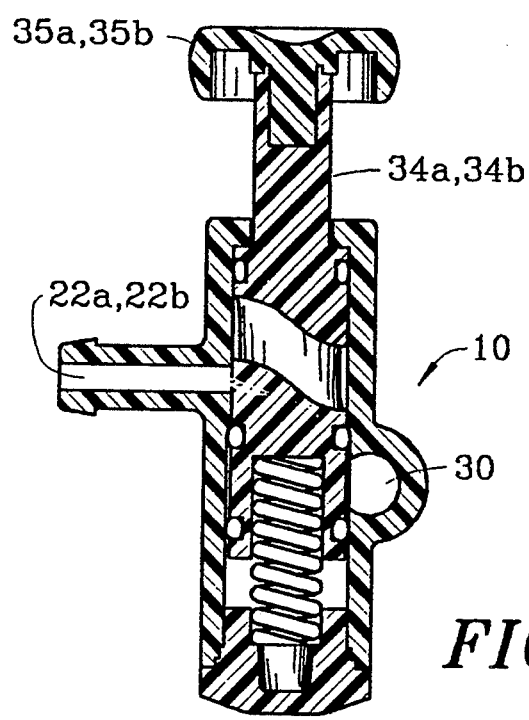
FIG. 7a is a sectional view of the valve and piston of the preferred embodiment of the present invention showing the present invention in its valve closed position.
Figure 8A:
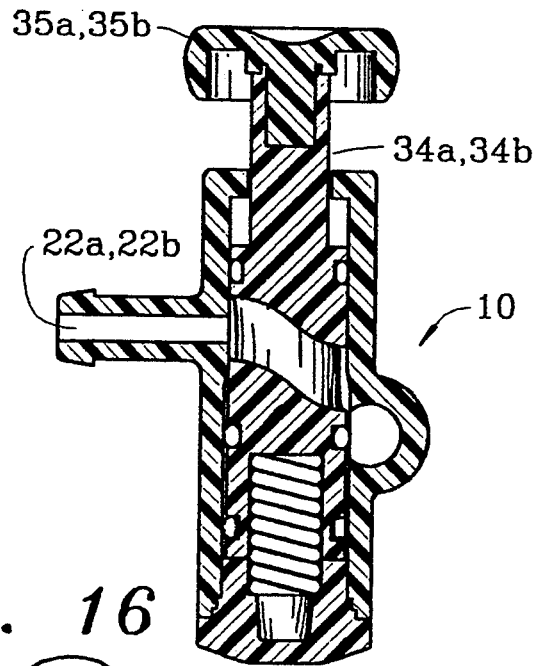
FIG. 8a is a sectional view of the valve and piston of the preferred embodiment of the present invention showing the present invention in its valve open position.
Figure 16:
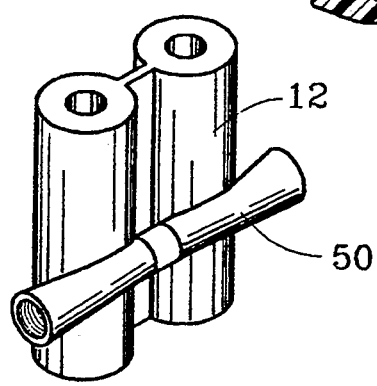
FIG. 16 is a perspective view of the present invention showing the alternative embodiment for the common conduit.
Figure 8:
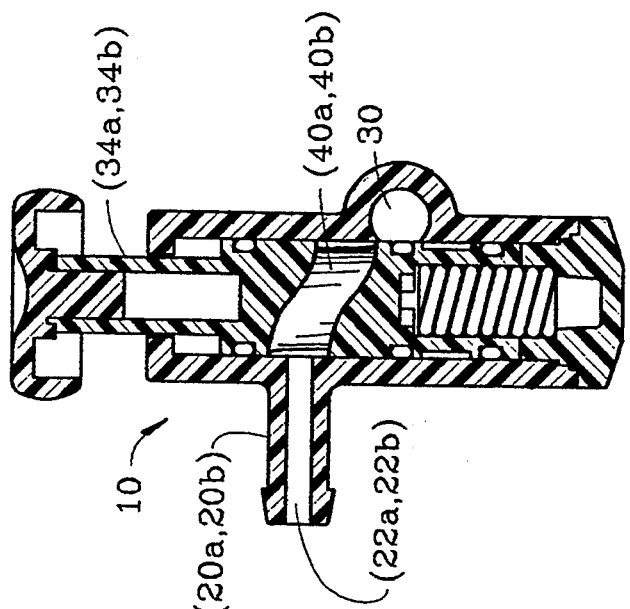
FIG. 8 is a sectional view of the valve and piston of the preferred embodiment of the present invention showing the piston in its partially depressed position.
Figure 7:
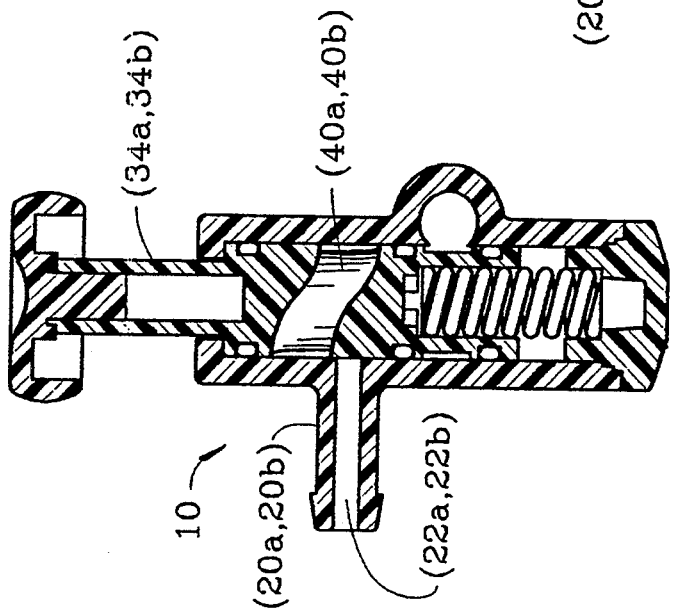
FIG. 7 is a sectional view of the valve and piston of the preferred embodiment of the present invention showing the piston in its normal position.

FIGS. 7, 7, 8 and 8a are cross sectional views of the preferred embodiment illustrating the piston (34a, 34b) in its normal position (FIGS. 7 and 7a), partially depressed position (FIG. 8) and its fully depressed position (FIG. 8a). Intersection between the common conduit channel (30) and the piston channel is clearly demonstrated, eliminating the need for an interconnecting channel and making plastic injection molding much easier by eliminating the need for a secondary drilling operation between the two conduits (The two core pins intersect to create the opening between the two conduits). It is seen from FIG. 8 and 8a that upon depression of piston (34a, 34b), the opening (40a, 40b,) in piston (34a, 34b, respectively) provides communication between fittings (20a, 20b) and conduit (30).

Figure 6:
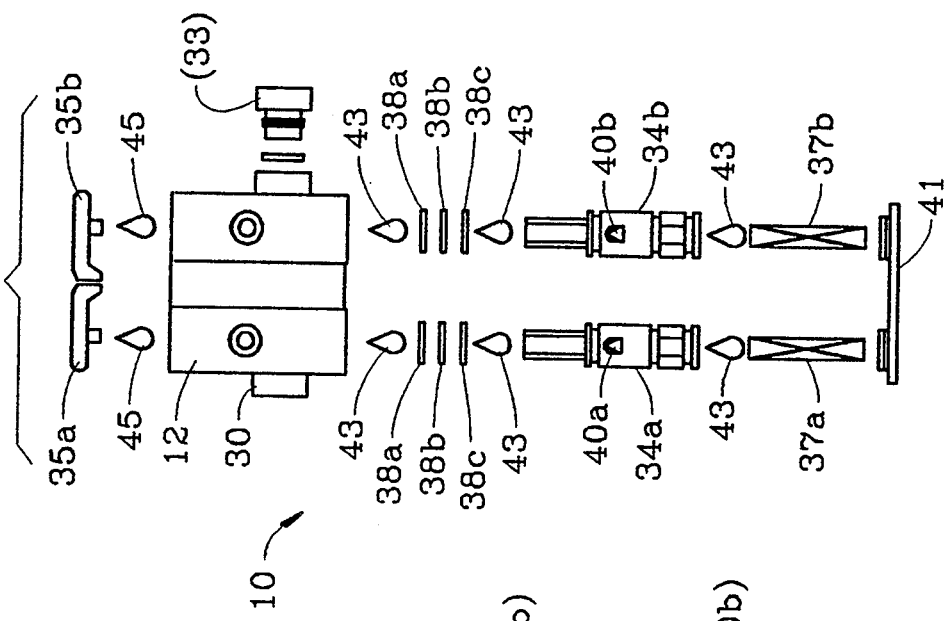
FIG. 6 is an exploded view of the preferred embodiment of the present invention illustrating the various components of the valve.

FIG. 6 illustrates the various components of valve (10) and more specifically shows the housing or body (12), buttons (35a, 35b), plug or cap (33), O-rings or seals (36a–c, 38a–c), pistons (34a, 34b), spring bias means (37a, 37b), base (41), lubrication (43) and adhesive (45).

Figure 14:
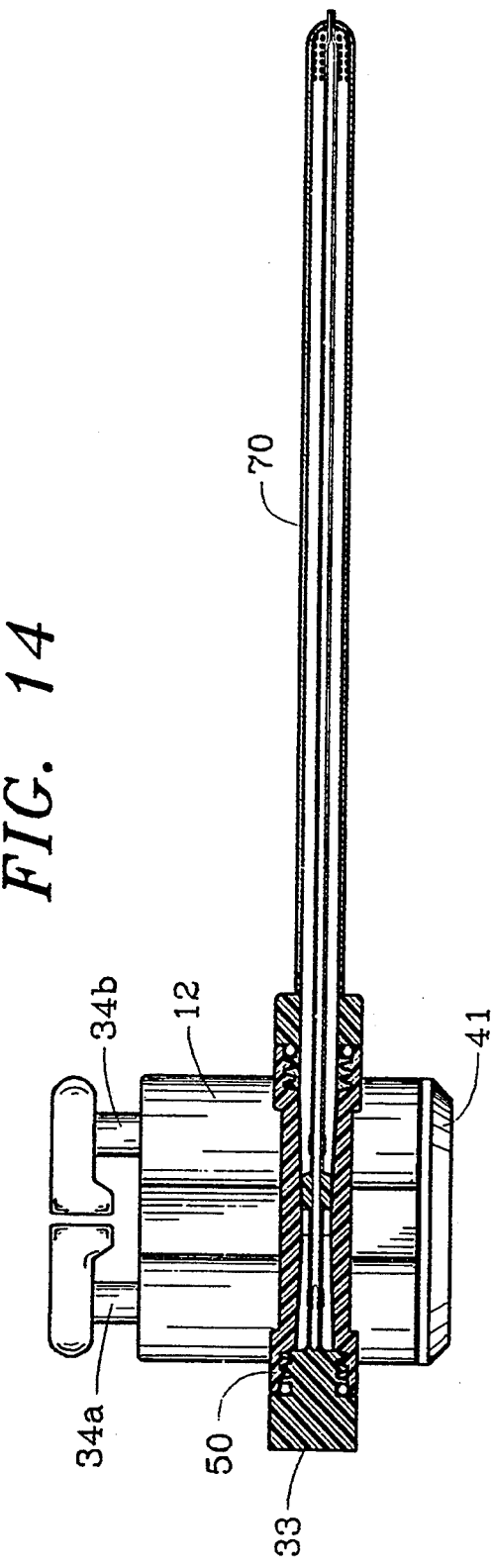
FIG. 14 is a cross sectional of the present invention connected to an interchangeable probe tip and having the alternative embodiment for the common conduit of FIG. 9.
Figure 15:
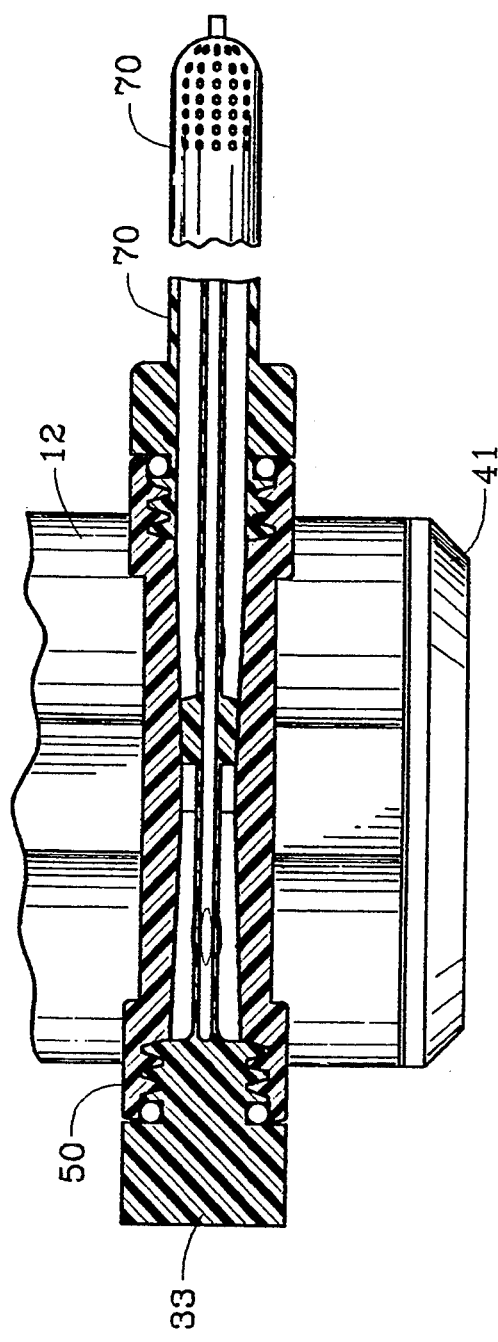
FIG. 15 is a sectional view of FIG. 14 showing the interchangeable probe tip connected to the conduit and an end of the probe tip.

FIGS. 9, 10, 14, 15 and 16 illustrate an alternative embodiment of the present invention where the shape of the common conduit (30) is changed to a substantially hourglass shape conduit (50). Hourglass conduit (50) allows for a frictional fit between an inner probe tip (70) and conduit (50). The hourglass shapes provides a wedge relationship between the inner cannula probe tip (70) and conduit (50) and assures correct position of the inner probe tip (70) within the valve (10). In addition, the wedged relationship achieved by the hourglass shape eliminates the need for extra seals and provides for a more fail safe seal in order to separate the features of suction and irrigation. FIGS. 14 and 15 illustrate a probe tip (70) connected to conduit (50) and also illustrates the wedge relationship between inner cannula tip of probe tip (70) and conduit (50) for separation between the suction and irrigation chambers. This hourglass design partitions off the suction chamber from the irrigation chamber and allows for concurrent suction and irrigation.

FIGS. 11–13 show an alternative embodiment for the piston. As seen from the figures, the modified flow design piston (60) can be substituted for piston (34a, 34b) of the primary embodiment. Piston (60) operates in a similar manner to piston (34a, 34b) to provide communication between fittings (22a, 22b) and conduit (30) or (50).

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A disposable irrigation control valve assembly, comprising:

a housing defining a plurality of valve chambers, each of said valve chambers having an elongated cylinder, a piston and means for reciprocating movement of said piston within said valve chamber, each of said valve chambers being further provided with an inlet orifice connectable to a source of vacuum or irrigation fluid and a second orifice formed in the cylinder wall and connected to a common conduit, the piston for each valve assembly being of a defined length relative to the length of the valve cylinder to allow for reciprocating movement of the pistons within their respective cylinders, each piston being further provided with an aperture, the size and shape of which being determined by the relative distance between the inlet and second orifices within the valve cylinder wall and, upon reciprocating movement of each piston within its respective cylinder, allowing for communication between the inlet and second orifices in said cylinder wall through the aperture in said pistons; and a common conduit formed in the value assembly at right angles relative to the cylinders of said valve body and communicating with each cylinder in said valve body through the second orifice in the cylinder wall thus allowing for simultaneous suction and irrigation, the common conduit having means for attaching a surgical probe permitting said simultaneous suction and irrigation.

2. The valve assembly of claim 1 wherein said means for attaching said surgical probe includes a pair of probe attachment members disposed at either end of said common conduit, wherein said housing being adapted for attachment of a probe to said housing at either one of said pair of probe attachment members to accommodate clinician preference.

3. The valve assembly of claim 1 wherein the aperture in the piston is of an essentially oval shape.

4. The valve assembly of claim 1 wherein the piston being further characterized as having a plurality of seals, one seal being positioned on the piston above the aperture to preclude fluid flow into the upper portion of the cylinder, a second seal positioned below the aperture in the piston to prevent the fluid communication between the inlet and outlet orifice of the cylinder prior to depression of the piston within the chamber and a third seal positioned below the second seal to prevent fluid flow from the chamber upon depression of the cylinder upon the establishment of fluid communication between the inlet and outlet orifices of said chamber.

5. The valve assembly of claim 1 wherein said means for attaching said surgical probe to the common means for readily interchanging a first surgical probe attached to said housing with a second surgical probe to allow a clinician to use a single housing with a plurality of surgical probes for various surgical procedures.

6. The valve assembly of claim 1 wherein said housing is symmetrical about a plane containing a wall that separates the valve chambers.

7. The valve assembly of claim 1 wherein said second orifice is axially offset from the inlet orifice.

8. The valve assembly of claim 1 wherein said common conduit is of an essentially hourglass shape.

9. The valve assembly of claim 1 wherein the means for attaching the surgical probe to the common conduit is adapted for connection to one of a plurality of interchangeable probes.

* * * * *

UNITED STATES PATENT AND TRADEMARK OFFICE
CERTIFICATE OF CORRECTION

PATENT NO.   : 5,391,145
DATED        : February 21, 1995
INVENTOR(S)  : James H. DORSEY, III It is certified that error appears in the above-indentified patent and that said Letters Patent is hereby corrected as shown below:

Claim 1,   Line 21:   "value" should be --valve--.
Claim 5,   Line 51:   "to the common" should be --includes--.

Signed and Sealed this

Fifteenth Day of April, 1997

Attest:

BRUCE LEHMAN

Attesting Officer         Commissioner of Patents and Trademarks